United States Patent
Ma et al.

(10) Patent No.: US 11,857,973 B2
(45) Date of Patent: *Jan. 2, 2024

(54) GENE SEQUENCING REACTION DEVICE, GENE SEQUENCING SYSTEM, AND GENE SEQUENCING REACTION METHOD

(71) Applicant: MGI Tech Co., LTD., Guangdong (CN)

(72) Inventors: Wei Ma, Guangdong (CN); Xun Xu, Shenzhen (CN); Jiabo Wu, Guangdong (CN); Ming Ni, Shenzhen (CN); Dong Wei, Guangdong (CN); Jiansheng Tang, Guangdong (CN)

(73) Assignee: MGI Tech Co., LTD., Guangdong (CN)

(*) Notice: Subject to any disclaimer, the term of this patent is extended or adjusted under 35 U.S.C. 154(b) by 64 days.

This patent is subject to a terminal disclaimer.

(21) Appl. No.: 17/569,903

(22) Filed: Jan. 6, 2022

(65) Prior Publication Data

US 2022/0126299 A1  Apr. 28, 2022

Related U.S. Application Data

(63) Continuation of application No. 16/635,347, filed as application No. PCT/CN2017/095512 on Aug. 1, 2017, now Pat. No. 11,241,692.

(51) Int. Cl.
*B01L 7/00* (2006.01)
*B01L 9/00* (2006.01)
*G01N 21/76* (2006.01)

(52) U.S. Cl.
CPC .................. *B01L 7/52* (2013.01); *B01L 9/52* (2013.01); *G01N 21/76* (2013.01); *B01L 2300/0819* (2013.01); *B01L 2300/185* (2013.01)

(58) Field of Classification Search
CPC ...... B01L 7/52; B01L 7/02; B01L 9/52; B01L 2300/0819; B01L 2300/185; C12M 1/34;
(Continued)

(56) References Cited

U.S. PATENT DOCUMENTS 11,241,692 B2 * 2/2022 Ma ........................... B01L 7/02
2005/0064535 A1   3/2005 Favuzzi et al.
(Continued)

FOREIGN PATENT DOCUMENTS

CN    1245218 A    2/2000
CN    1726386 A    1/2006
(Continued)

OTHER PUBLICATIONS

Extended European Search Report for Application No. 17920580.2, dated Feb. 9, 2021.
(Continued)

*Primary Examiner* — Michael L Hobbs
(74) *Attorney, Agent, or Firm* — Wolf, Greenfield & Sacks, P.C.

(57) ABSTRACT

A gene sequencing reaction device, a gene sequencing system and a gene sequencing reaction method. The gene sequencing reaction device includes: a supporting platform; a dipping container disposed on the supporting platform, wherein the dipping container has a dipping reaction area, and the dipping reaction area is configured to hold a chemical reagent for gene sequencing reaction, so as to dip a sequencing chip having a DNA sample loading structure on the surface and having a DNA sample loaded thereon in the chemical reagent to perform a gene sequencing reaction; a temperature control apparatus, configured to control the temperature of the chemical reagent in the dipping reaction area; and a transfer apparatus, configured to insert the
(Continued)

sequencing chip into the dipping reaction area or pull out the sequencing chip from the dipping reaction area.

18 Claims, 11 Drawing Sheets

(58) Field of Classification Search
CPC .......... C12Q 1/6874; C12Q 2523/303; C12Q 2527/113; C12Q 2565/625; G01N 35/00029
See application file for complete search history.

(56) References Cited

U.S. PATENT DOCUMENTS

| | | |
|---|---|---|
| 2006/0094108 A1 | 5/2006 | Yoder et al. |
| 2009/0137414 A1 | 5/2009 | Drmanac et al. |
| 2009/0253194 A1 | 10/2009 | Kambara et al. |
| 2011/0136135 A1 | 6/2011 | Larsen et al. |
| 2013/0150266 A1 | 6/2013 | Tisone et al. |
| 2014/0273088 A1 | 9/2014 | Winther |
| 2021/0138473 A1 | 5/2021 | Ma et al. |

FOREIGN PATENT DOCUMENTS

| | | |
|---|---|---|
| CN | 101555452 A | 10/2009 |
| CN | 104849121 A | 8/2015 |
| CN | 205133580 U | 4/2016 |
| CN | 205473785 U | 8/2016 |
| DE | 102011104147 A1 | 12/2012 |
| DE | 102011108363 A1 | 1/2013 |
| WO | WO 2013/073610 A1 | 5/2013 |

OTHER PUBLICATIONS

International Search Report and Written Opinion for Application No. PCT/CN2017/095512, dated Apr. 19, 2018.
International Preliminary Report on Patentability for Application No. PCT/CN2017/095512, dated Feb. 13, 2020.
Machine Translation of CN104849121A.

* cited by examiner

GENE SEQUENCING REACTION DEVICE, GENE SEQUENCING SYSTEM, AND GENE SEQUENCING REACTION METHOD

CROSS-REFERENCE TO RELATED APPLICATIONS

This Application is a Continuation of U.S. application Ser. No. 16/635,347 (now U.S. Pat. No. 11,241,692), filed Jan. 30, 2020, entitled "GENE SEQUENCING REACTION DEVICE, GENE SEQUENCING SYSTEM, AND GENE SEQUENCING REACTION METHOD", which is a national stage filing under 35 U.S.C. 371 of International Patent Application Serial No. PCT/CN2017/095512, filed Aug. 1, 2017, entitled "GENE SEQUENCING REACTION DEVICE, GENE SEQUENCING SYSTEM, AND GENE SEQUENCING REACTION METHOD". The contents of these applications are incorporated herein by reference in their entireties.

FIELD OF THE INVENTION

The present disclosure relates to the field of gene sequencing technology, in particular to a gene sequencing reaction device, a gene sequencing system and a gene sequencing reaction method.

BACKGROUND OF THE INVENTION

According to the current technological level, DNA sample molecules need to be loaded onto a sequencing chip prior to gene sequencing (also referred to as DNA sequencing), then a gene sequencing reaction is further completed to add nucleotides to a sequencing reaction template, and the sequence of a gene may be detected by detecting the type of the added nucleotides.

The Chinese utility model patent CN205133580U provides a currently widely used sequencing chip, the chip is provided with an internal flow channel, different chemical reagents are injected into the flow channel from an inlet and are discharged from an outlet after flow through the flow channel, and whether the loading or sequencing of the DNA sample needs to implement the above process. In this conventional sequencing chip, after the DNA sample is loaded onto the surface of the flow channel, a sequencing reagent is injected to cause a sequencing chemical reaction of the DNA sample, which has the following disadvantages:
  (1) the chemical reagents may only be used once, resulting in a high sequencing cost;
  (2) the flow rates of chemical reagents in the flow channel are not uniform, and there are also positions where the chemical reagents cannot flow to, this results in an uneven and insufficient chemical reaction, so that the problem of gene sequencing errors is generated easily; and furthermore, the flowing chemical reagents are easy to flush away the DNA molecules that have been loaded onto the surface of the flow channel of the chip;
  (3) the pressure generated by the chemical reagents in the flow channel easily causes a collapse phenomenon on the surface of the chip, and the deformation on the surface of the chip increases the error rate of the DNA sequencing; and
  (4) the available area of a silicon surface of the chip only includes the surface in the flow channel, and other parts cannot be effectively utilized, such that a silicon chip cannot be utilized to the utmost extent.

SUMMARY OF THE INVENTION

A first aspect of the present disclosure provides a gene sequencing reaction device, comprising: a supporting platform; a dipping container disposed on the supporting platform, wherein the dipping container has a dipping reaction area configured to hold a chemical reagent for gene sequencing reaction, so as to dip a sequencing chip having a DNA sample loading structure on the surface and having a DNA sample loaded thereon in the chemical reagent to perform a gene sequencing reaction; a temperature control apparatus, configured to control the temperature of the chemical reagent in the dipping reaction area; and a transfer apparatus, configured to insert the sequencing chip into the dipping reaction area or pull out the sequencing chip from the dipping reaction area.

In some embodiments, the gene sequencing reaction device comprises a plurality of dipping containers; and/or, the dipping container comprises a plurality of dipping reaction areas isolated from each other.

In some embodiments, the dipping container comprises an overflow port.

In some embodiments, the temperature control apparatus comprises a temperature control portion and a water bath kettle, the water bath kettle is configured to hold liquid capable of transferring heat, the dipping container is disposed in the water bath kettle, and the temperature control portion is configured to control the temperature of the liquid in the water bath kettle to control the temperature of the chemical reagent in the dipping reaction area.

In some embodiments, the gene sequencing reaction device comprises: a chip supplying storage apparatus, configured to contain the sequencing chip on which the gene sequencing reaction is about to be performed; and/or, a chip unloading storage apparatus, configured to contain the sequencing chip on which the gene sequencing reaction has been completed.

In some embodiments, the chip supplying storage apparatus and/or the chip unloading storage apparatus comprises: a chip storage box, wherein the top of the chip storage box is open and is provided with a slot and a drain hole, the slot is configured to position and contain the sequencing chip, and the drain hole is formed in a bottom wall of the chip storage box to discharge the liquid in the chip storage box; and, a liquid storage box disposed below the drain hole for receiving the liquid discharged from the drain hole.

In some embodiments, the gene sequencing reaction device comprises a container cover, and the container cover is configured to be capable of being opened and closed and covered on the dipping container to prevent the evaporation of the chemical reagent.

In some embodiments, the container cover comprises a plurality of cover bodies, each of the cover bodies is correspondingly disposed with one or more dipping reaction areas to prevent the evaporation of the chemical reagent in the corresponding dipping reaction areas, and at least one of the cover bodies is opened and closed independently relative to other cover bodies.

In some embodiments, the gene sequencing reaction device comprises a cover overturning mechanism, and the cover overturning mechanism is in driving connection with the container cover to drive the container cover to open and close.

In some embodiments, the transfer apparatus comprises a connecting portion configured to be connected with the sequencing chip, and a movement mechanism being in driving connection with the connecting portion to change a working position of the connecting portion.

In some embodiments, the plurality of dipping reaction areas are disposed in one or more rows along a lateral direction; the movement mechanism comprises a lateral movement mechanism, a longitudinal movement mechanism and a vertical movement mechanism, the longitudinal movement mechanism is disposed on the supporting platform, the lateral movement mechanism is disposed on the longitudinal movement mechanism, the vertical movement mechanism is disposed on the lateral movement mechanism, the connecting portion is disposed on the vertical movement mechanism, the longitudinal movement mechanism drives the lateral movement mechanism to perform longitudinal movement, the lateral movement mechanism drives the vertical movement mechanism to perform lateral movement, and the vertical movement mechanism drives the connecting portion to perform vertical movement.

In some embodiments, the gene sequencing reaction device comprises a chip holding apparatus, the chip holding apparatus comprises one or more chip mounting positions, and the sequencing chip is mounted on the chip mounting position so as to move the sequencing chip by moving the chip holding apparatus.

In some embodiments, the DNA sample loading structures are provided on both sides of the sequencing chip are provided with; and the chip mounting position comprises a chip mounting opening, the sequencing chip is mounted in the chip mounting opening, and the chip mounting opening is a through opening with both open sides.

In some embodiments, the chip holding apparatus comprises a chip framework, the chip mounting position is disposed on the chip framework, the surface of the chip framework is a hydrophobic surface, and/or, a lower end of the chip framework is gradually tapered from top to bottom.

In some embodiments, the chip holding apparatus comprises a chip framework, one or more chip mounting positions are disposed on the chip framework, and an upper end of the chip framework is provided with a jaw fitting opening; the transfer apparatus comprises a clamping jaw connected with the chip framework and a movement mechanism in driving connection with the clamping jaw to change the working position of the clamping jaw, the clamping jaw comprises a positioning frame and a clamping block, the positioning frame is connected with the movement mechanism, the clamping block is movably disposed on the positioning frame, the positioning frame is provided with a positioning hole for inserting the upper end of the chip framework, and the clamping jaw is clamped with the jaw fitting opening of the chip framework inserted into the positioning hole so as to clamp the chip framework.

In some embodiments, the gene sequencing reaction device comprises a controller, wherein the controller is coupled with the temperature control apparatus to control the temperature of the chemical reagent; and/or, the controller is coupled with the transfer apparatus to control the dipping time and/or dipping sequence of the sequencing chip in the dipping reaction area.

In some embodiments, the gene sequencing reaction device comprises the sequencing chip, and the surface of the sequencing chip is provided with the DNA sample loading structure.

In some embodiments, the gene sequencing reaction device comprises a protective cover, and the dipping container is disposed in the protective cover.

In some embodiments, the gene sequencing reaction device comprises an air blowing apparatus, configured to blow off the chemical reagent on the surface of the sequencing chip and/or the surface of the chip holding apparatus on which the sequencing chip is mounted.

A second aspect of the present disclosure provides a gene sequencing system, comprising a DNA sample loading device and a gene sequencing reaction device, wherein the gene sequencing reaction device is the gene sequencing reaction device according to any one of the items in the first aspect of the present disclosure.

A third aspect of the present disclosure provides a gene sequencing reaction method, comprising: adding a chemical reagent for gene sequencing reaction into a dipping reaction area of a dipping container; controlling the temperature of the chemical reagent in the dipping reaction area; and dipping a sequencing chip having a DNA sample loading structure on the surface and having a DNA sample loaded thereon in the chemical reagent for a predetermined time, and taking out the sequencing chip.

In some embodiments, the gene sequencing reaction method comprises: adding different chemical reagents for gene sequencing reaction into a plurality of dipping reaction areas, and sequentially dipping the sequencing chip into the plurality of dipping reaction areas for a predetermined time according to a predetermined sequence.

Based on the gene sequencing reaction device provided by the present disclosure, the dipping container has the dipping reaction area, and the dipping reaction area is configured to hold the chemical reagent for gene sequencing reaction and is configured to dip the sequencing chip having the DNA sample loading structure on the surface and having the DNA sample loaded thereon to perform the gene sequencing reaction; the temperature control apparatus is configured to control the temperature of the dipping reaction area; and the transfer apparatus is configured to insert the sequencing chip into the dipping reaction area or pull out the sequencing chip from the dipping reaction area. By adopting the gene sequencing reaction device, the gene sequencing reaction may be achieved in a dipping manner.

Other features of the present disclosure and the advantages thereof will become apparent from the following detailed description of exemplary embodiments of the present disclosure with reference to the drawings.

BRIEF DESCRIPTION OF THE DRAWINGS

The drawings described herein are used for providing a further understanding of the present disclosure and constitute a part of the present application. The exemplary embodiments of the present disclosure and descriptions thereof are used for explaining the present disclosure, but do not constitute improper limitations to the present disclosure. In the drawings.

DETAILED DESCRIPTION OF THE EMBODIMENTS

Figure 1:
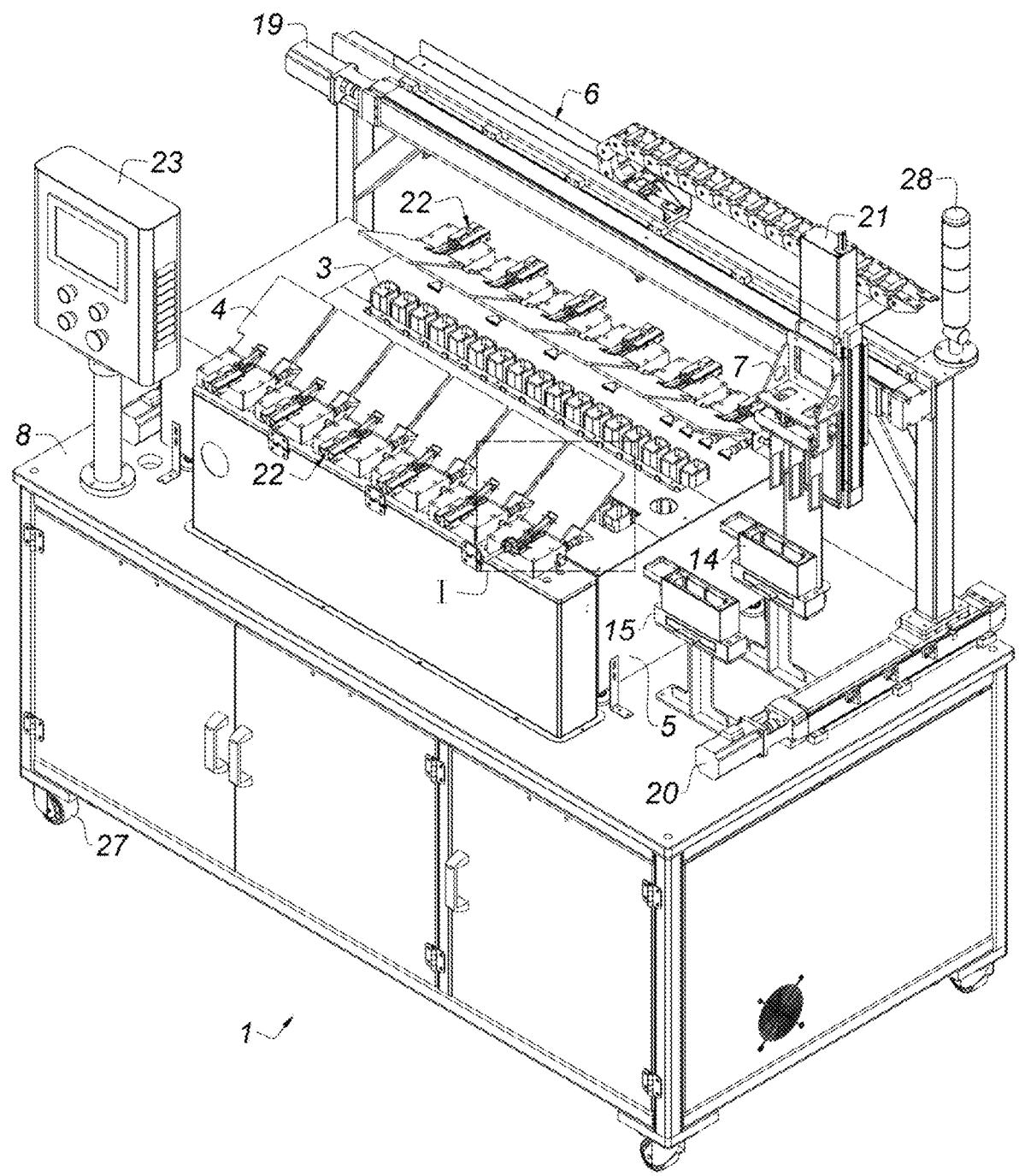
FIG. 1 is a schematic perspective view of a gene sequencing reaction device in an embodiment of the present disclosure.

A clear and complete description of technical solutions in the embodiments of the present disclosure will be given below, in combination with the drawings in the embodiments of the present disclosure. Apparently, the embodiments described below are merely a part, but not all, of the embodiments of the present disclosure. The following description of at least one exemplary embodiment is merely illustrative and is in no way used as any limitation to the present disclosure and its application or use. All of other embodiments, obtained by those of ordinary skill in the art based on the embodiments in the present disclosure without any creative effort, fall into the protection scope of the present disclosure.

Unless otherwise specified, the relative arrangement of the components and steps, numerical expressions and numerical values set forth in these embodiments are not intended to limit the scope of the present disclosure. In the meantime, it should be understood that the dimensions of various parts shown in the drawings are not drawn in the actual scale relationship for the convenience of description. Techniques, methods and devices known to those of ordinary skill in the relevant art may not be discussed in detail, but where appropriate, the techniques, methods and devices should be considered as a part of the authorized specification. In all of examples shown and discussed herein, any specific value should be construed as illustrative only and not as a limitation. Accordingly, other examples of the exemplary embodiments may have different values. It should be noted that: similar reference numerals and letters indicate similar items in the following drawings, therefore, once an item is defined in one drawing, it is not required to be further discussed in the subsequent drawings.

In the description of the present disclosure, it should be understood that, the terms "first", "second" and the like are used for defining components and parts, and are merely for the convenience of distinguishing the corresponding components and parts, and unless otherwise stated, the above words have no special meaning, and thus cannot be construed as limiting the protection scope of the present disclosure.

In the description of the present disclosure, it should be understood that, orientation or position relationships indicated by orientation words such as "front, back, upper, lower, left, right", "lateral, longitudinal, vertical, horizontal" and "top, bottom" and the like are generally orientation or position relationships shown on the basis of the drawings, and are merely for the convenience of describing the present disclosure and simplifying the description, in the absence of opposite statement, these orientation words do not indicate or imply that the referred apparatuses or elements must have specific orientations or must be constructed and operated in specific orientations, and thus cannot be construed as limiting the protection scope of the present disclosure; and the orientation words "inside and outside" refer to the inside and outside of the contours of the components themselves.

Figure 2:
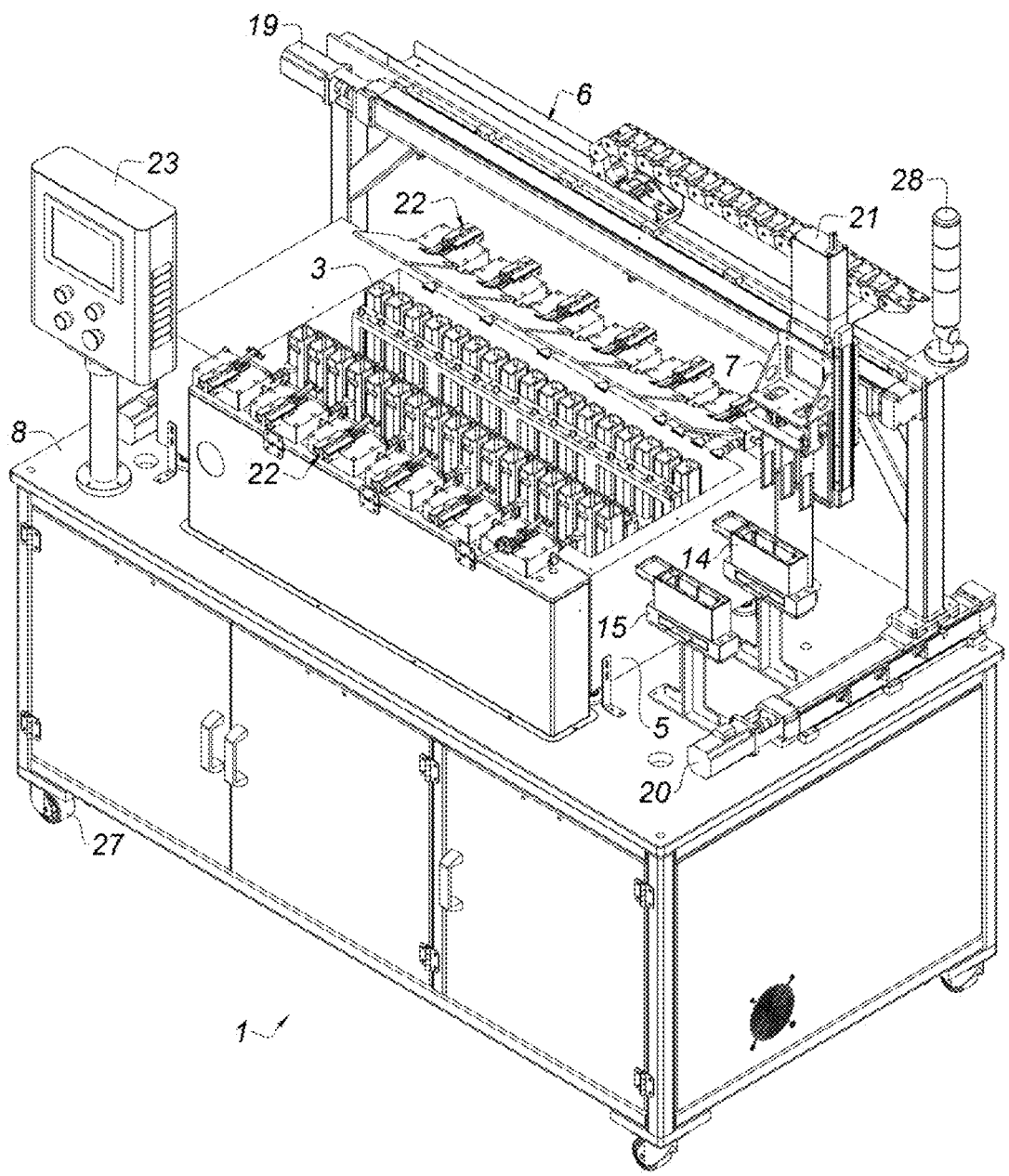
FIG. 2 is a schematic perspective view of the gene sequencing reaction device in FIG. 1 after a container cover is removed.
Figure 3:
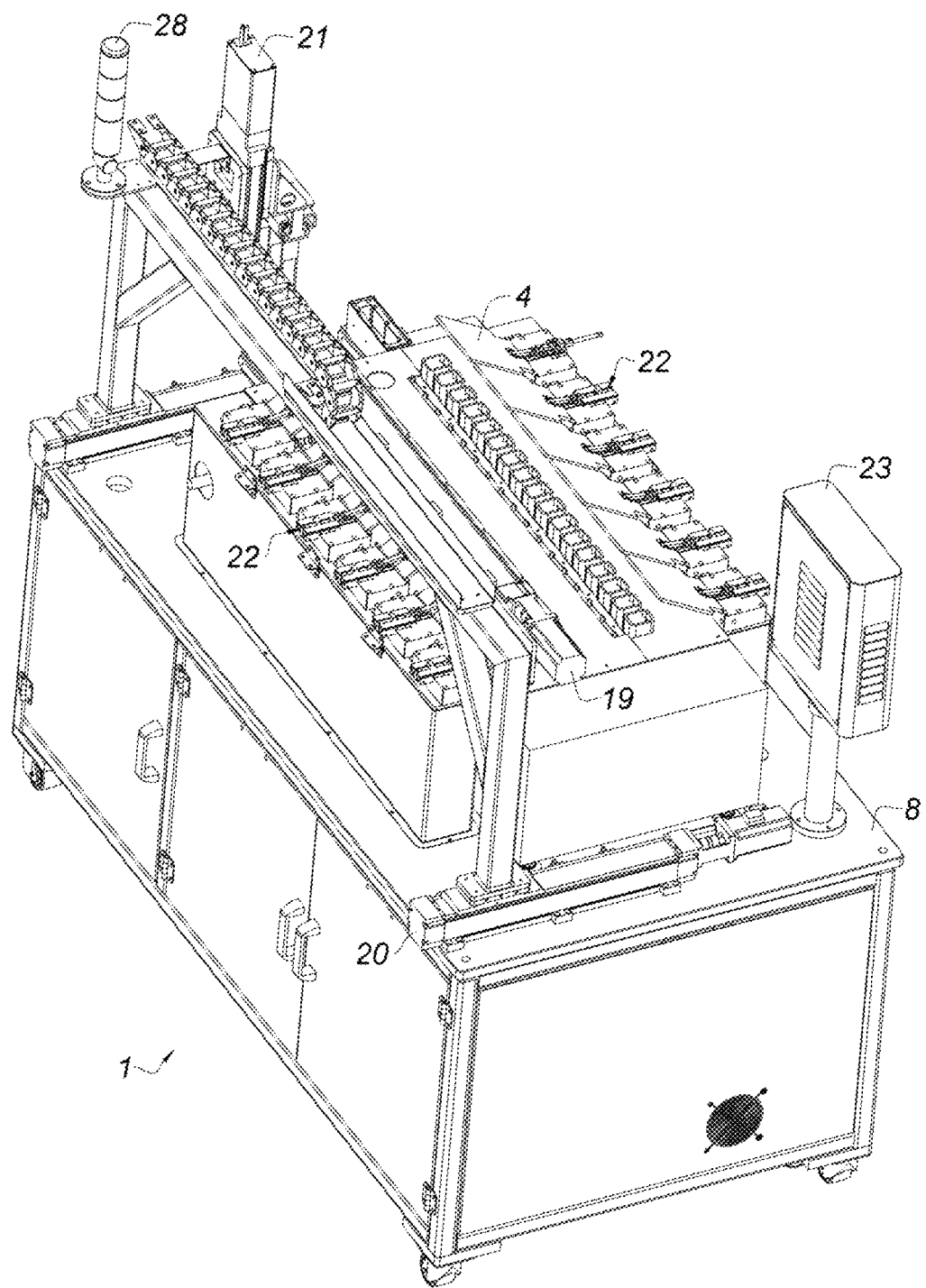
FIG. 3 is a schematic perspective view of another angle of the gene sequencing reaction device as shown in FIG. 1.
Figure 4:
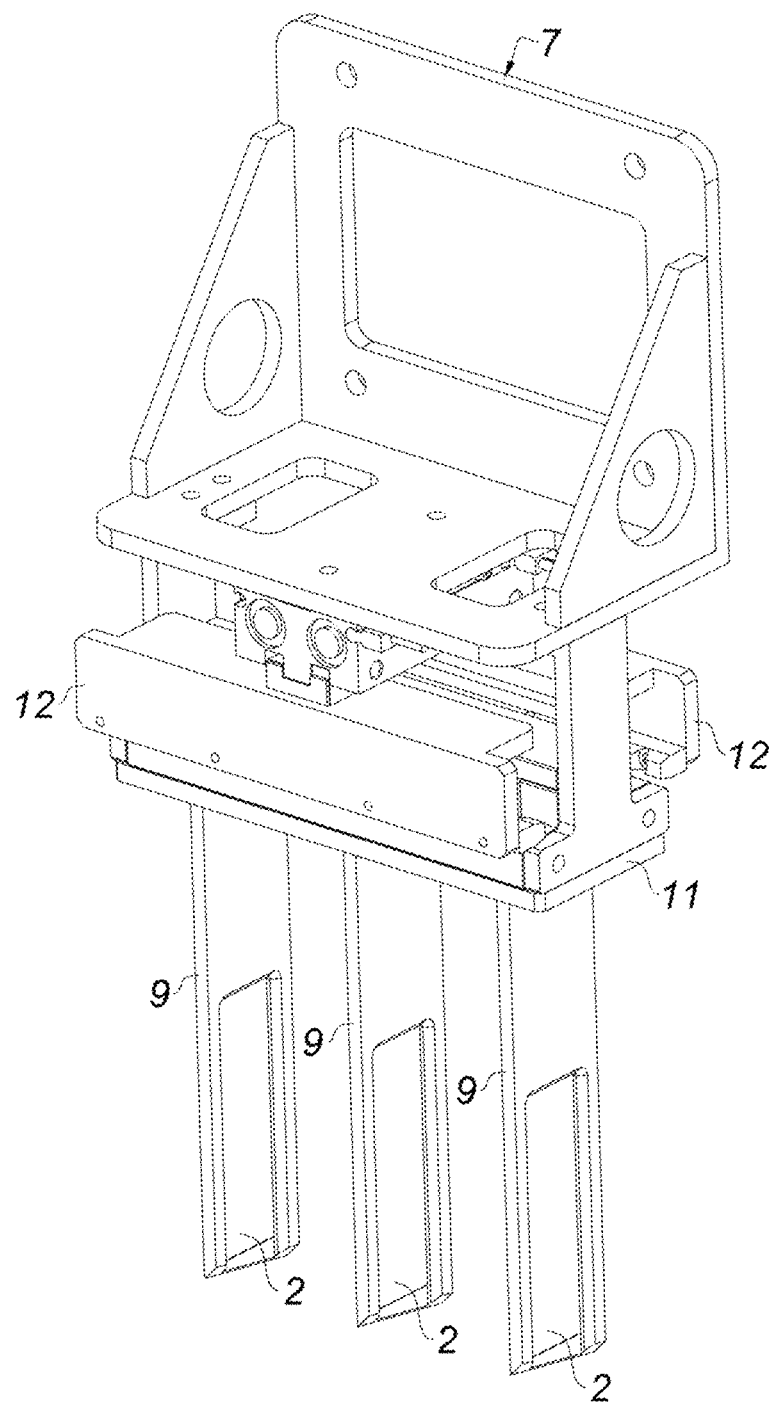
FIG. 4 is a schematic perspective view of a clamping jaw of a transfer apparatus, a sequencing chip and a chip holding apparatus of the gene sequencing reaction device as shown in FIG. 1.

A "lateral direction" used in the following description refers to a left-right direction of the gene sequencing reaction device as shown in FIG. 1 to FIG. 3, a "longitudinal direction" refers to a front-back direction of the gene sequencing reaction device as shown in FIG. 1 to FIG. 3, and a "vertical direction" refers to an up and down direction of the gene sequencing reaction device as shown in FIG. 1 to FIG. 3.

FIG. 1 to FIG. 11 show the structure of a gene sequencing reaction device 1 in an embodiment of the present disclosure. As shown in FIG. 1 to FIG. 11, the embodiment of the present disclosure discloses a gene sequencing reaction device 1. The gene sequencing reaction device 1 includes a supporting platform 8, a dipping container, a temperature control apparatus 5, and a transfer apparatus 6. The dipping container is disposed on the supporting platform 8. The dipping container has a dipping reaction area, and the dipping reaction area is used for holding a chemical reagent for gene sequencing reaction and dipping a sequencing chip 2 having a DNA sample loading structure on the surface and having a DNA sample loaded thereon in the chemical reagent to perform a gene sequencing reaction. The temperature control apparatus 5 is configured to control the temperature of the chemical reagent in the dipping reaction area. The transfer apparatus 6 is configured to insert the sequencing chip 2 into the dipping reaction area or pull out the sequencing chip from the dipping reaction area.

The DNA sample in the present embodiment is a sequencing reaction template, and labeled nucleotides may be added to the sequencing reaction template.

The gene sequencing reaction device 1 provided by the present disclosure may realize the gene sequencing reaction in a dipping manner. The sequencing chip 2 is dipped in the chemical reagents in different dipping reaction areas to complete various steps required for the sequencing reaction. The chemical reagent in the dipping reaction area may be reused, thereby reducing the cost of consumables. There is no problem of uneven liquid flow rate in the dipping manner, and bubbles are unlikely to be generated on the surface of the sequencing chip 2, so that a more uniform and sufficient chemical reaction may be ensured. The sequencing chip 2 is subjected to uniform pressure and uniform heating in the dipping reaction area, thereby generating no deformation. No complicated fluid system is needed, few parts and components are used, the assembly is easy, and the manufacturing cost is low. Multiple sequencing chips 2 may be dipped at the same time, thereby having the advantages of high throughput. The gene sequencing reaction device 1 may be automatically controlled by the controller 23, so that automated operation may be achieved.

The embodiment of the present disclosure will be described in detail below in combination with FIG. 1 to FIG. 11.

As shown in FIG. 1 to FIG. 11, the gene sequencing reaction device 1 of the embodiment of the present disclosure includes a sequencing chip 2, a dipping container, a temperature control apparatus 5, a transfer apparatus 6, a chip holding apparatus, an chip supplying storage apparatus 14, a chip unloading storage apparatus 15, a container cover 4, a cover overturning mechanism 22, an air blowing apparatus 25, a controller 23, and a supporting platform 8.

The surface of the sequencing chip 2 is provided with a DNA sample loading structure, and before the gene sequencing reaction is performed, a DNA sample has been loaded on the DNA sample loading structure of the sequencing chip 2. In the present embodiment, the sequencing chip 2 is a silicon chip, and linkers capable of capturing DNA molecules are preset on surfaces of both sides of the silicon chip. After a series of chemical reactions, the DNA molecules may be captured by these linkers and eventually adhered to the surface of the silicon chip. The linkers may be formed, for example, by modifying the surface of the silicon chip with amino group. During the gene sequencing reaction, the DNA sample is always attached to the sequencing chip 2.

The so called DNA sample in the present embodiment may be a nanosphere molecule disclosed in U.S. Pat. No. 8,445,197 B2, which may also be referred to as DNB. A genomic DNA is fragmented at first, a sequence of linkers is added then, and cyclizing is performed to form a single-stranded circular DNA, the single-stranded circular DNA is amplified to 2-3 orders of magnitudes by using the rolling circle amplification technology to form the DNB.

The dipping container has a dipping reaction area, and the dipping reaction area is used for holding a chemical reagent for gene sequencing reaction and dipping a sequencing chip 2 having a DNA sample loading structure on the surface and having a DNA sample loaded thereon in the chemical reagent to perform the gene sequencing reaction. The sequencing chip 2 is dipped in the chemical reagent for gene sequencing reaction in the dipping reaction area to complete the steps of the gene sequencing reaction. The temperature control apparatus 5 may control the temperature of the chemical reagent in the dipping reaction area to provide a suitable temperature condition for the gene sequencing reaction.

In the present embodiment, the gene sequencing reaction device 1 includes a plurality of dipping containers. As shown in FIG. 1 to FIG. 3, the dipping container is specifically a dipping cylinder 3. Each dipping cylinder 3 has a dipping reaction area. A plurality of dipping cylinders 3 are disposed on the temperature control apparatus 5. The temperature control apparatus 5 is disposed on the supporting platform 8. The transfer apparatus 6 may insert the sequencing chip 2 into the dipping cylinder 3 and pull out the sequencing chip 2 from the dipping cylinder 3. In the present embodiment, each dipping cylinder 3 is filled with a chemical reagent, and different dipping cylinders are filled with chemical reagents required for each gene sequencing link. After the transfer apparatus 6 clamps the sequencing chip 2 for dipping in the dipping cylinders 3 for a predetermined time, nucleotides may be added to the DNA sample (the sequencing reaction template) of the sequencing chip 2. Thereafter, the sequencing chip 2 is placed on an external optical imaging device for imaging, and then the type of the added nucleotides may be detected. The sequence of the gene may be read by continuously circulating the above steps.

In other embodiments not shown, the dipping cylinders 3 may also be grouped, and each group of dipping cylinders 3 is filled with a chemical reagent.

Referring to FIG. 1 to FIG. 3, in the present embodiment, the gene sequencing reaction device 1 includes two rows of dipping cylinders 3 disposed laterally, and each row includes 17 dipping cylinders 3.

In other embodiments not shown, the dipping container may also include a plurality of dipping reaction areas isolated from one another, and each or each group of dipping reaction areas is filled with a chemical reagent.

Figure 10:
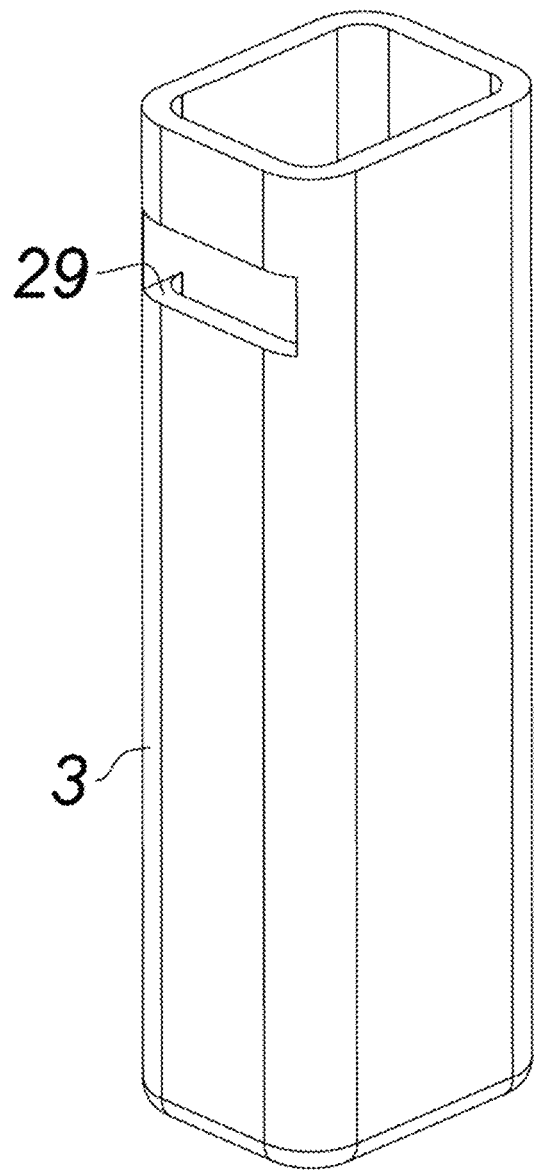
FIG. 10 is a schematic perspective view of a dipping cylinder of the gene sequencing reaction device as shown in FIG. 1.

As shown in FIG. 10, in the present embodiment, the dipping cylinder 3 includes an overflow port 29. When the liquid in the dipping cylinder 3 exceeds a certain water level, it overflows from the overflow port 29, so that the liquid level in the dipping cylinder 3 may be prevented from being excessively high.

The temperature control apparatus 5 is configured to control the temperature of the chemical reagent in the dipping reaction area. The temperature control apparatus 5 is disposed on the supporting platform 8, and the dipping container is disposed on the supporting platform 8 through the temperature control apparatus 5.

In the present embodiment, as shown in FIG. 1 to FIG. 3, the temperature control apparatus 5 includes a temperature control portion and a water bath kettle. The water bath kettle is configured to hold liquid capable of transferring heat. The dipping container is disposed in the water bath kettle. The temperature control portion controls the temperature of the liquid in the water bath kettle to control the temperature of the chemical reagent in the dipping container.

In the present embodiment, the temperature control portion is a heat exchange tube disposed in the wall of the water bath kettle, and the heat exchange tube may input heat to the liquid in the water bath kettle or absorb heat from the liquid in the water bath kettle, so that the heat conduction liquid in the water bath kettle may be heated or cooled down accordingly.

By inputting or outputting the heat to the wall of the water bath kettle or the liquid in the water bath kettle, the heat conduction liquid in the water bath kettle may be heated or cooled down accordingly, and the dipping cylinder 3 is dipped in the heat conduction liquid, so that the temperature of the chemical reagent in the dipping cylinder 3 may be controlled. By using the liquid as a heat conducting medium, the temperature of the chemical reagent in each dipping cylinder 3 may be controlled more uniformly. Furthermore, the temperature of the chemical reagent is more stable and is unlikely to change quickly.

In other embodiments not shown, a direct temperature control manner of directly heating or cooling the dipping cylinder 3 or the liquid therein may also be adopted by a temperature controller (for example, a Peltier temperature controller), but the direct temperature control manner is prone to a phenomenon of uneven heating and cooling compared with the indirect temperature control manner of the water bath kettle.

The chip supplying storage apparatus 14 is configured to contain the sequencing chip 2 on which the gene sequencing reaction is about to be performed. The chip unloading storage apparatus 15 is configured to contain the sequencing chip 2 on which the gene sequencing reaction has been completed.

Figure 8:
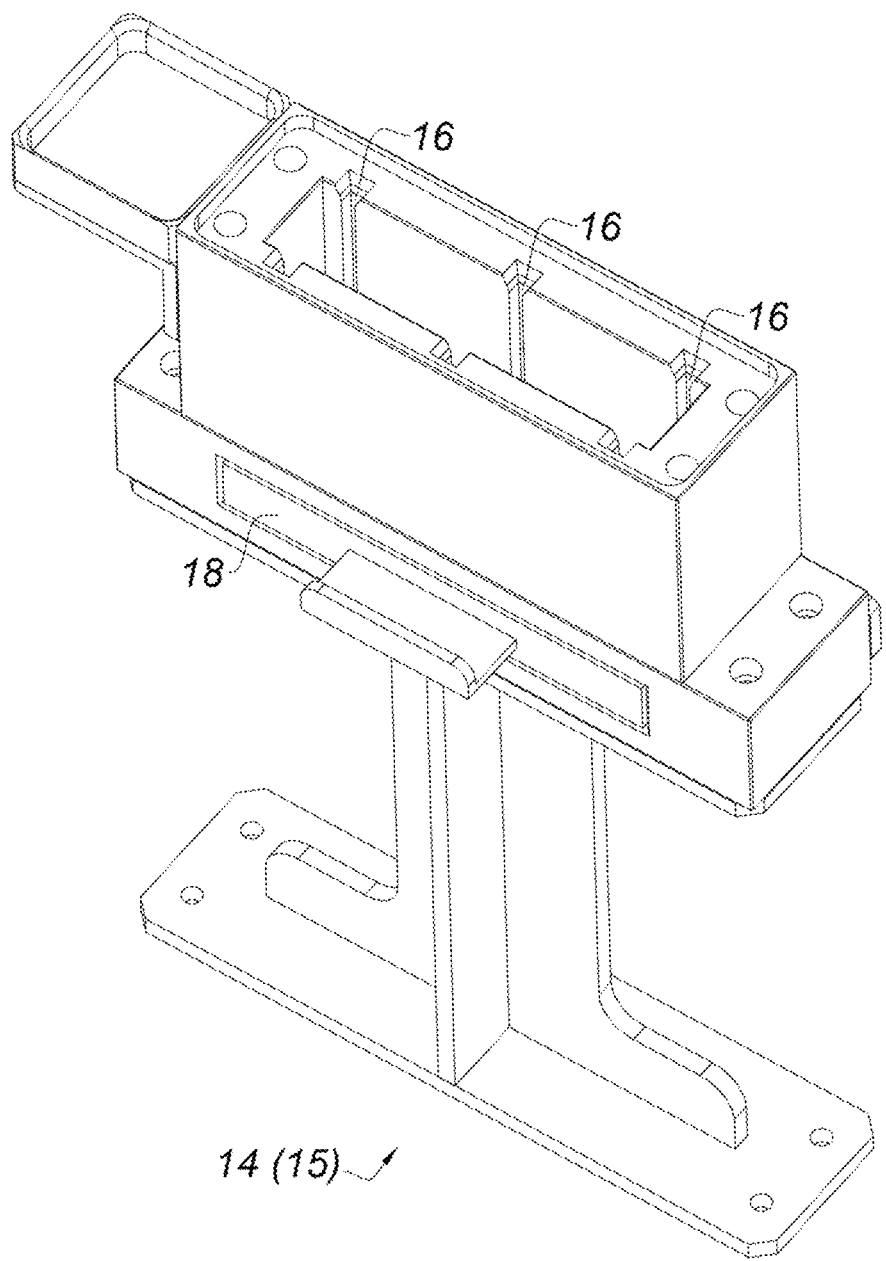
FIG. 8 is a schematic perspective view of a chip supplying storage apparatus (or a chip unloading storage apparatus) of the gene sequencing reaction device as shown in FIG. 1.
Figure 9:
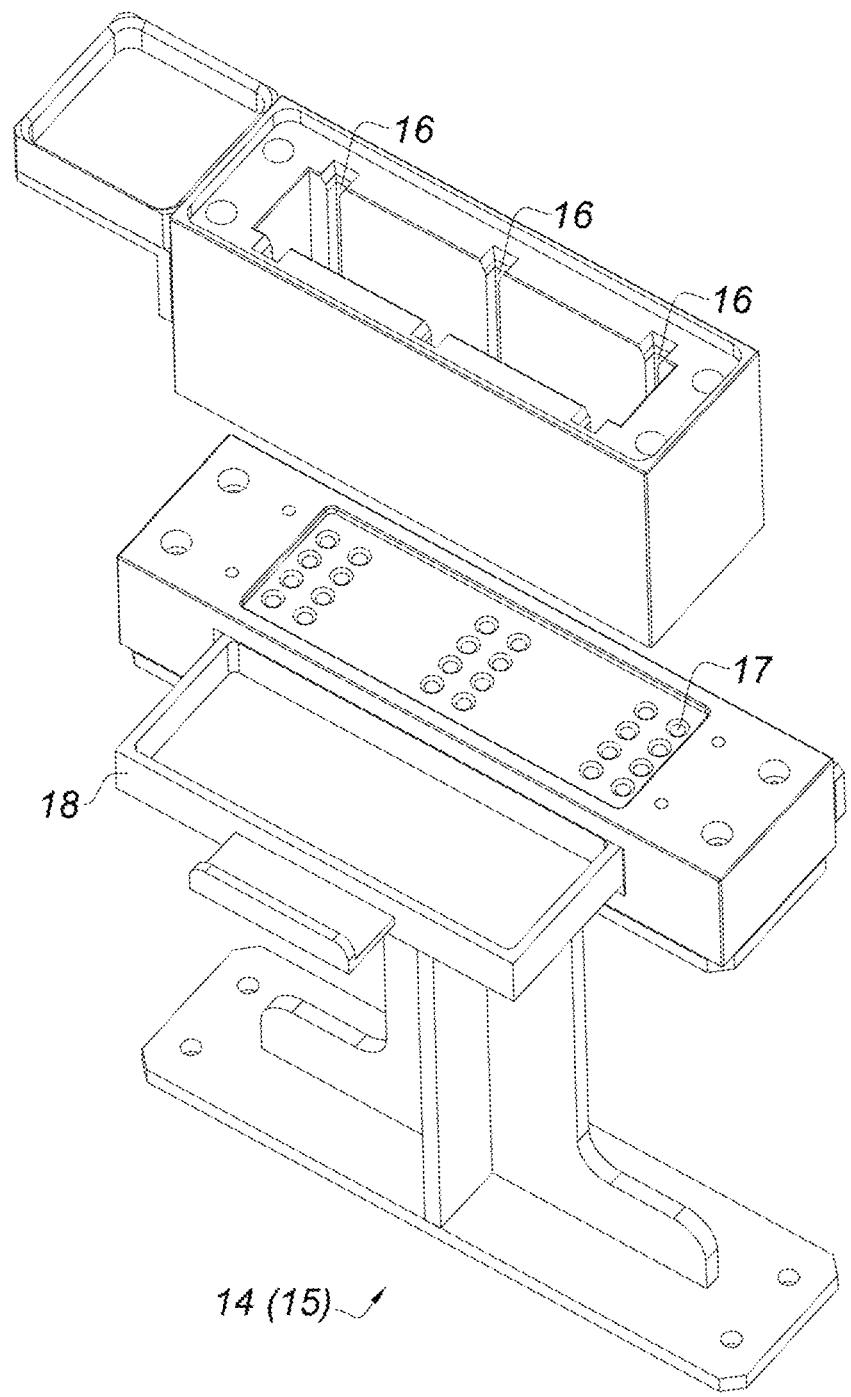
FIG. 9 is a schematic perspective view of the chip supplying storage apparatus (or the chip unloading storage apparatus) as shown in FIG. 8.

As shown in FIG. 8 and FIG. 9, in the present embodiment, each of the chip supplying storage apparatus 14 and the chip unloading storage apparatus 15 includes a chip storage box and a liquid storage box 18. The top of the chip storage box is open and is provided with a slot 16 and a drain hole 17. The slot 16 is formed in an inner surface of a side wall of the chip storage box configured to position and contain the sequencing chip 2. The drain hole 17 is formed in a bottom wall of the chip storage box for discharging the liquid in the chip storage box. In the present embodiment, the drain hole 17 may drain the chemical reagent flowing down from the surfaces of the chip framework 9 and the sequencing chip 2.

In the present embodiment, in a gene sequencing reaction process, the sequencing chip 2 is mounted on the chip framework 9, and the sequencing chip 2 is moved by moving the chip framework 9. The slot 16 is configured to position and contain the chip framework 9 so as to position and contain the sequencing chip 2 through the chip framework 9. The chip framework 9 is inserted into the slot 16 to position and contain the sequencing chip 2 thereon in the chip storage box.

The number of slots 16 of the chip supplying storage apparatus 14 and the chip unloading storage apparatus 15 optionally corresponds to the number of positioning holes 13 on a clamping jaw 7 which will be described later, to ensure that the clamping jaw 7 accurately clamp and place the chip framework 9. As shown in FIG. 4 to FIG. 7, in the present embodiment, the number of positioning holes 13 of the clamping jaw 7 is 3; and as shown in FIG. 8 and FIG. 9, the number of slots 16 of the chip supplying storage apparatus 14 and the chip unloading storage apparatus 15 is also 3.

The liquid storage box 18 is disposed below the drain hole 17 for receiving the liquid discharged from the drain hole 17. The liquid storage box 18 in the present embodiment is made into a drawer type box body, which may be taken out to pour the liquid, when the liquid storage box 18 is filled with liquid or the use of the gene sequencing reaction device 1 is stopped.

It should be noted that, although each of the chip supplying storage apparatus 14 and the chip unloading storage apparatus 15 of the gene sequencing reaction device 1 in the present embodiment include the chip storage box and the liquid storage box 18, in other embodiments not shown, the specific structures of the chip supplying storage apparatus 14 and the chip unloading storage apparatus 15 may also be set in other manners. The structures of the chip supplying storage apparatus 14 and the chip unloading storage apparatus 15 may be the same or different.

In addition, neither the chip supplying storage apparatus 14 nor the chip unloading storage apparatus 15 is necessary. For example, after the sequencing chip 2 is mounted on the chip holding apparatus, it may be directly placed in the dipping reaction area corresponding to a first reaction link of the gene sequencing reaction, and the chip supplying storage apparatus 14 is not disposed. As another example, after the sequencing chip 2 completes the sequencing reaction, it may be directly sent to the external optical imaging device for imaging, and the chip unloading storage apparatus 15 is not disposed.

The container cover 4 is configured to be capable of being opened and closed and covered on the dipping container to prevent the evaporation of the chemical reagent.

Figure 11:
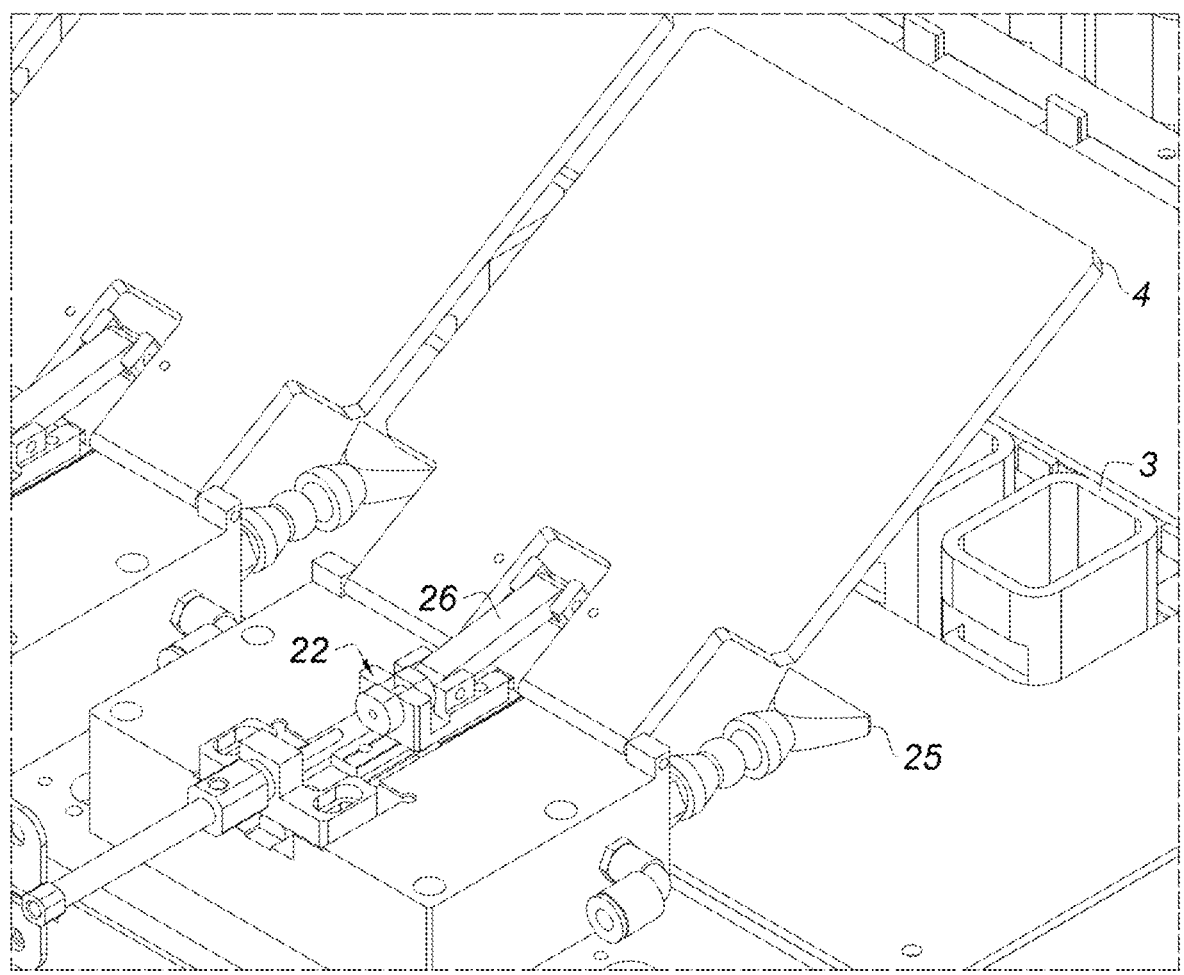
FIG. 11 is a schematic amplified view of a portion I of the gene sequencing reaction device as shown in FIG. 1.

As shown in FIG. 1, FIG. 2 and FIG. 11, optionally, the container cover 4 comprises a plurality of cover bodies, and each of the cover bodies is correspondingly disposed with one or more dipping reaction areas to prevent the evaporation of the chemical reagent in the corresponding dipping reaction areas. At least one of the cover bodies may be opened and closed independently relative to other cover bodies. In the present embodiment, corresponding to the two rows of dipping cylinders 3, the container cover 4 includes two rows of cover bodies, and each row includes 6 cover bodies. And each cover body covers a plurality of dipping cylinders 3.

The cover overturning mechanism 22 is in driving connection with the container cover 4 to drive the container cover 4 to open and close. As shown in FIG. 1 to FIG. 3, the cover overturning mechanism 22 is disposed on the supporting platform 8. Referring to FIG. 11, the cover overturning mechanism 22 includes a push-pull rod 26 correspondingly arranged with the cover body, the push-pull rod 26 is connected with the cover body of the container cover 4, when the push-pull rod 26 pulls the cover body, the cover body is opened, and when the push-pull rod 26 pushes the cover body, the cover body is closed.

The transfer apparatus 6 is configured to insert the sequencing chip 2 into the dipping reaction area or pull out the sequencing chip 2 from the dipping reaction area. In the present embodiment, the transfer apparatus 6 is configured to move the sequencing chip 2 to insert the sequencing chip 2 into each dipping reaction area or pull out the sequencing chip from each dipping reaction area.

The transfer apparatus 6 of the present embodiment may move the sequencing chip 2 in any dipping cylinder 3 into another dipping cylinder 3.

In the present embodiment, the sequencing chip 2 on which the gene sequencing reaction is about to be performed may be contained in the slot 16 of the chip supplying storage apparatus 14 by another external transfer apparatus, and the sequencing chip 2 may also be manually contained in the slot 16 of the chip supplying storage apparatus 14. Similarly, the sequencing chip 2 on which the gene sequencing reaction has been completed may be taken away by another external transfer apparatus, and the sequencing chip 2 may also be manually taken away.

By disposing the transfer apparatus 6, the automation degree of the gene sequencing reaction device 1 may be improved, the error rate caused by the manual operation may be reduced, and the dipping sequence and the dipping time may also be accurately controlled by cooperation with the controller 23, thereby facilitating the high-quality completion of the gene sequencing reaction.

In the present embodiment, the transfer apparatus 6 is configured to move the sequencing chip 2, and includes a connecting portion connected with the sequencing chip 2, and a movement mechanism that is in driving connection with the connecting portion to change a working position of the connecting portion.

The transfer apparatus 6 is mounted on the supporting platform 8. In other embodiments not shown, the transfer apparatus 6 may also be mounted on other supports, as long as the function of connecting and moving the sequencing chip 2 may be achieved.

In the present embodiment, as shown in FIG. 1 to FIG. 3, the movement mechanism includes a lateral movement mechanism 19, a longitudinal movement mechanism 20 and a vertical movement mechanism 21. The longitudinal movement mechanism 20 is disposed on the supporting platform 8. The lateral movement mechanism 19 is disposed on the longitudinal movement mechanism 20. The vertical movement mechanism 21 is disposed on the lateral movement mechanism 19. The connecting portion is disposed on the vertical movement mechanism 21. The longitudinal movement mechanism 21 drives the lateral movement mechanism 19 to perform longitudinal movement. The lateral movement mechanism 19 drives the vertical movement mechanism 21 to perform lateral movement. The vertical movement mechanism 21 drives the connecting portion to perform vertical movement. The connecting portion in the present embodiment includes a clamping jaw 7 for clamping the sequencing chip 2.

As described above, the plurality of dipping cylinders 3 are arranged in two rows along the lateral direction. By the combined use of the lateral movement mechanism 19, the longitudinal movement mechanism 20 and the vertical movement mechanism 21, it may be ensured that the clamping jaw 7 may insert the sequencing chip 2 into and pull out the sequencing chip 2 from any one of the dipping cylinders 3.

In addition, the dipping cylinders 3 may also be arranged in a ring shape, at this time, the movement mechanism may include a rotating mechanism. The connecting portion may also be in other forms, for example, a vacuum chuck, an electromagnetic chuck or the like that cooperates with the chip holding apparatus for supporting the sequencing chip 2.

In addition, although the movement of the sequencing chip 2 between different dipping cylinders 3 is realized by moving the sequencing chip 2 through the movement mechanism and the connecting portion in the present embodiment, in other embodiments not shown, a required position relationship change between the sequencing chip 2 and the dipping cylinder may be achieved just by purely moving the dipping container or simultaneously moving the dipping container and the sequencing chip 2.

The chip holding apparatus is configured to hold the sequencing chip 2, so that the sequencing chip 2 moves along with the chip holding apparatus. The chip holding apparatus includes one or more connecting portions 24, and the sequencing chip 2 is mounted on the chip mounting position so as to move the sequencing chip 2 by moving the chip holding apparatus.

By disposing the chip holding apparatus, on one hand, the pollution caused by directly operating the sequencing chip 2 may be reduced, and on the other hand, a plurality of sequencing chips 2 are simultaneously moved by the chip holding apparatus as needed, and the plurality of sequencing chips 2 keep a predetermined interval, thereby improving the throughput of the sequencing chip 2.

In the present embodiment, surfaces on both sides of the sequencing chip 2 are provided with the DNA sample loading structures. As shown in FIG. 4 to FIG. 7, the chip mounting position includes a chip mounting opening, the sequencing chip 2 is mounted in the chip mounting opening, and the chip mounting opening is a through opening with both open sides. Due to such setting, both surfaces of the sequencing chip 2 may be dipped, so that the number of DNA sample molecules loaded by the single sequencing chip 2 may be increased.

In addition, the chip framework 9 is transferred between different dipping cylinders 3. In order to reduce the cross contamination between different chemical reagents as much as possible, it is generally required that the chip framework 9 is transferred into the next dipping cylinder 3 after all liquid remaining on the surface of the chip framework 9 drops. In order to speed up the dripping speed of the liquid on the surface of the chip framework 9, as shown in FIG. 4 to FIG. 7, in the present embodiment, a lower end of the chip framework 9 is gradually tapered from top to bottom. In an alternative embodiment, the surface of the chip framework 9 may be set as a hydrophobic surface. Of course, the chip framework 9 may be set as the hydrophobic surface while the lower end of the chip framework 9 is gradually tapered from top to bottom, thereby achieving faster dripping of the chemical reagent.

Figure 5:
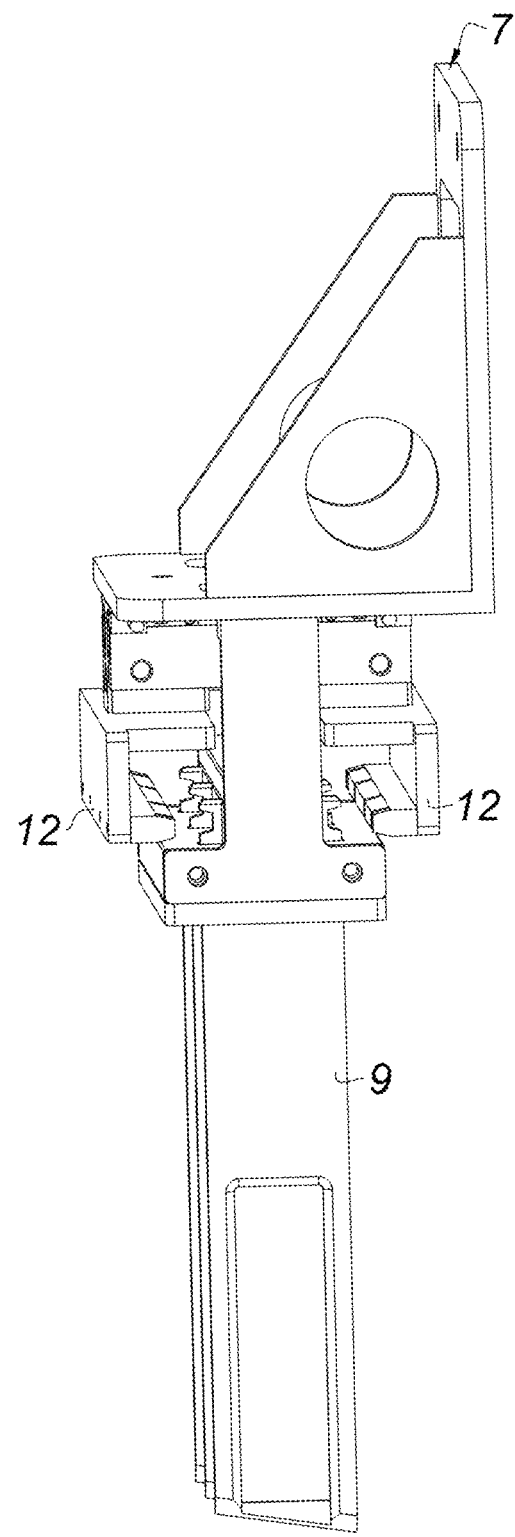
FIG. 5 is a schematic perspective view of another angles of the clamping jaw of the transfer apparatus, the sequencing chip and the chip holding apparatus as shown in FIG. 4.
Figure 6:
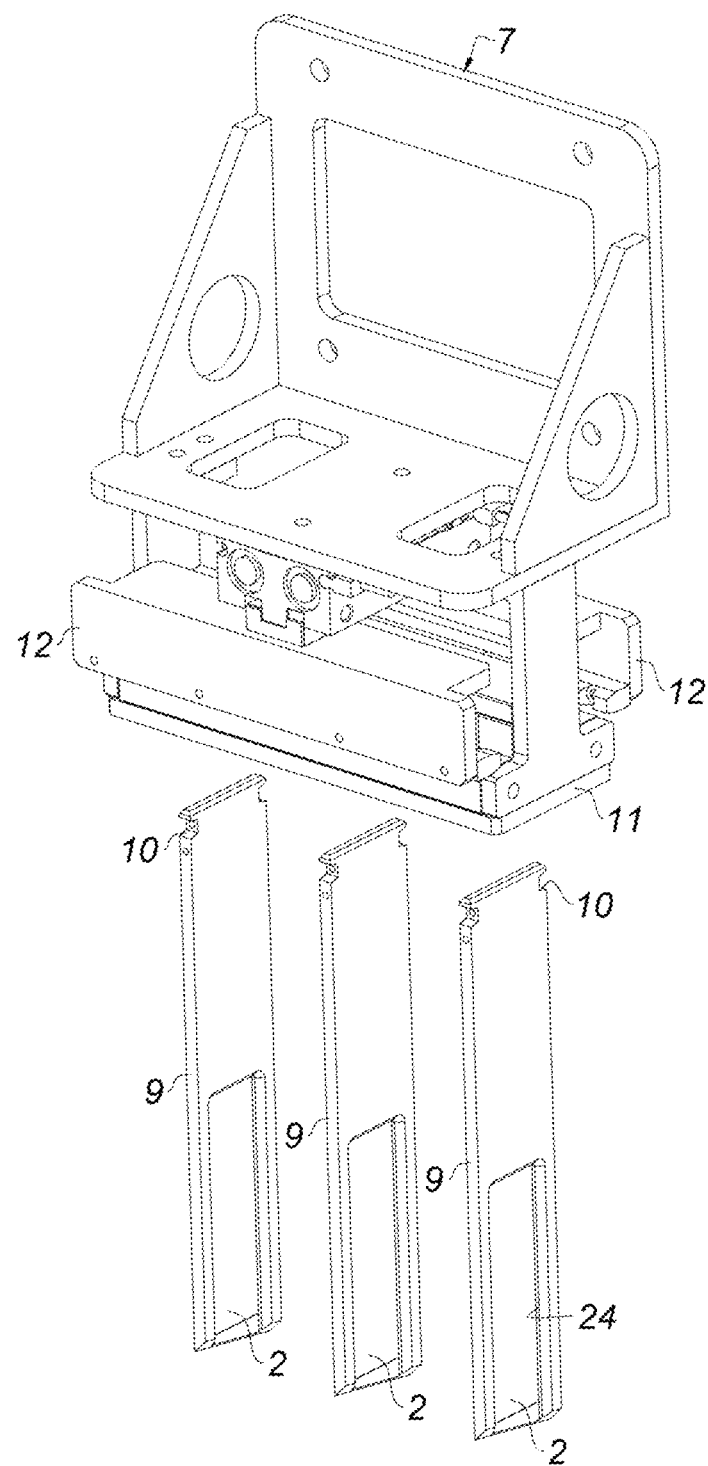
FIG. 6 is a schematic exploded view of the clamping jaw of the transfer apparatus, the sequencing chip and the chip holding apparatus as shown in FIG. 4.
Figure 7:
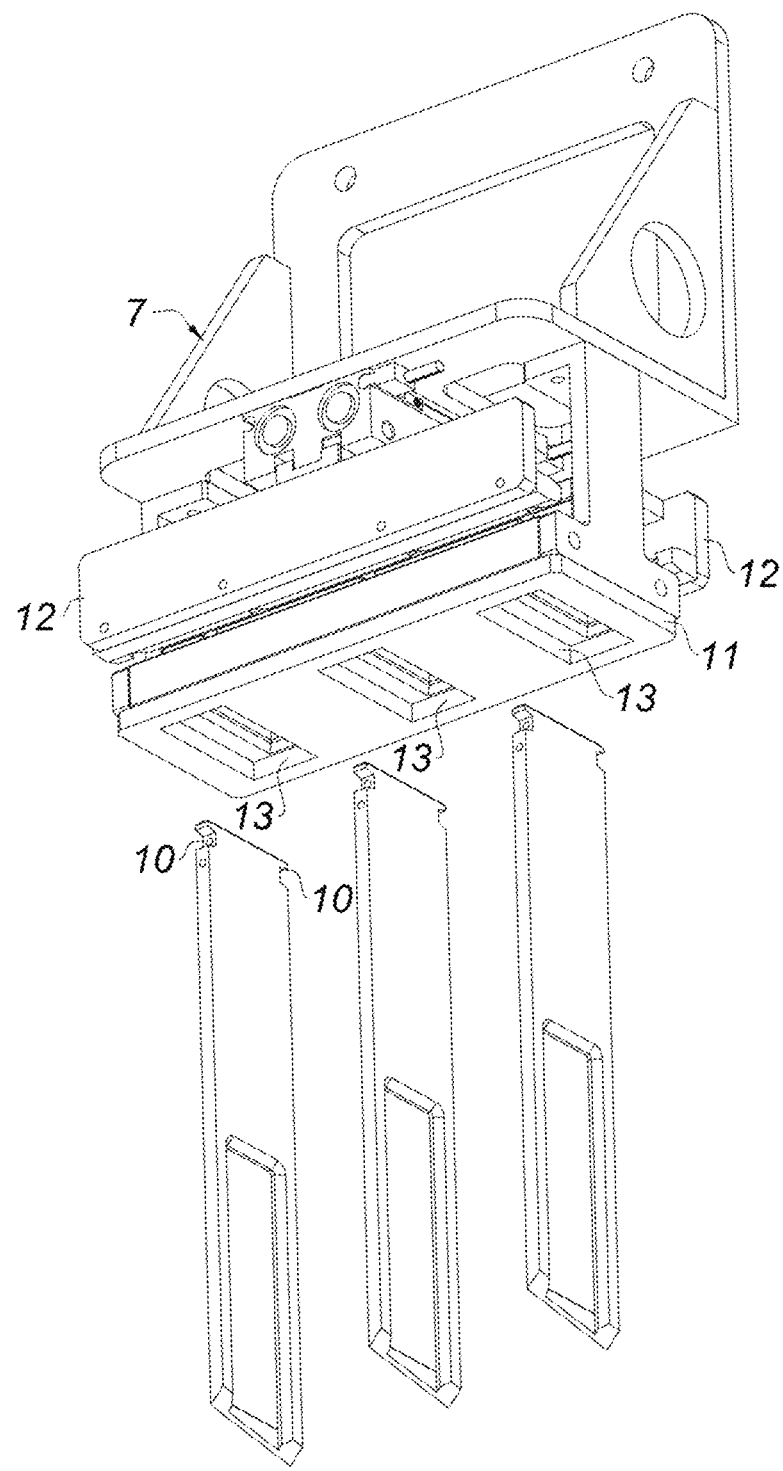
FIG. 7 is a schematic exploded view of another angles of the clamping jaw of the transfer apparatus, the sequencing chip and the chip holding apparatus as shown in FIG. 4.

As shown in FIG. 5 to FIG. 7, an upper end of the chip framework 9 is provided with a jaw fitting opening 10; and a movement mechanism of the transfer apparatus 6 is in driving connection with the clamping jaw 7 to change the working position of the clamping jaw 7, and the clamping jaw 7 is connected with the chip framework 9.

In the present embodiment, the clamping jaw 7 includes a positioning frame 11 and a clamping block 12, the positioning frame 11 is connected with the movement mechanism, the clamping block 12 is movably disposed on the positioning frame 11, the positioning frame 11 is provided with a positioning hole 13 for inserting the upper end of the chip framework 9, and the clamping jaw 7 is clamped with the jaw fitting opening 10 of the chip framework 9 inserted into the positioning hole 13 so as to clamp the chip framework 9.

As shown in FIG. 4 to FIG. 7, each chip framework 9 is provided with two jaw fitting openings 10 oppositely. The clamping jaw 7 is also correspondingly provided with two opposite clamping blocks 12. The clamping blocks 12 are located above the positioning hole 13. After the chip framework 9 passes through the positioning hole 13 upward, the two clamping blocks 12 move toward each other and are respectively clamped in the two jaw fitting openings 10 of the chip framework 9, so as to fix the chip framework 9 in the positioning hole 13. The positioning frame 11 of the present embodiment is designed with three positioning holes 13, and the three positioning holes 13 are arranged equidistantly. In other embodiments not shown, the number of positioning holes 13 may be set to be more or less, for example, may be set as 1, 2, 4, 5 and the like, so as to simultaneously operate the corresponding number of sequencing chips 2. The number and positions of the dipping reaction areas and the number and positions of the slots 16 vary depending on the number of positioning holes 13.

In the present embodiment, the clamping jaw 7 of the transfer apparatus 6 indirectly holds the sequencing chip 2 through the chip holding apparatus to realize the connection between the transfer apparatus 6 and the sequencing chip 2. Through the indirect clamping of the sequencing chip 2, cross contamination generated after the clamping jaw 7 clamps different sequencing chips 2 may be prevented. In addition, the clamping jaw 7 indirectly clamps the sequencing chip 2 by clamping the chip framework 9, so a clamping structure only needs to be processed on the chip framework 9, and the clamping structure does not need to be processed on the sequencing chip 2, thereby reducing the processing cost of the sequencing chip 2, and maximally utilizing the surface area of the sequencing chip 2.

Of course, in other embodiments not shown, the transfer apparatus 6 and the sequencing chip 2 may also be connected by directly clamping the sequencing chip 2 via the clamping jaw 7.

Optionally, the gene sequencing reaction device 1 includes a protective cover, and the dipping container is disposed in the protective cover. The sequencing reaction process may be completely open if environmental conditions permit, for example, during operation in a sterile environment. However, in many cases, in order to avoid external interference, the sequencing reaction process needs to be carried out in a closed environment, the dipping container is located in the protective cover to provide a closed reaction environment to ensure the quality of the gene sequencing reaction. The transfer apparatus 6 may also be disposed in the protective cover or not as needed.

The air blowing apparatus 25 is configured to blow off the chemical reagent on the surface of the sequencing chip 2 and/or the surface of the chip holding apparatus on which the sequencing chip is mounted. In the present embodiment, the air blowing apparatus 25 is configured to blow off the residual chemical reagent on the surfaces of the sequencing chip 2 and the chip framework 9. By blowing off the residual chemical reagent on the surfaces of the sequencing chip 2 and the chip framework 9, the cross contamination generated when the sequencing chip 2 is dipped in the next dipping reaction area may be avoided as much as possible.

Referring to FIG. 11, in the present embodiment, the air blowing apparatus 25 includes a nozzle. The nozzle is configured to eject a gas, and the ejected gas blows off the residual chemical reagent on the surfaces of the sequencing chip 2 and the chip framework 9.

The controller 23 is configured to control and monitor the work of the gene sequencing reaction device 1. In the present embodiment, the controller 23 is coupled with the temperature control apparatus 5 to control the temperature of the chemical reagent, and is also coupled with the transfer apparatus 6 to control the dipping time and/or dipping sequence of the sequencing chip 2 in the dipping reaction area.

In the present embodiment, the controller 23 is a built-in controller and is disposed on the supporting platform 8. In other embodiments not shown, an external controller may also be coupled with the gene sequencing reaction device 1 to control and monitor the work of the gene sequencing reaction device 1.

By controlling the temperature control apparatus 5 and the transfer apparatus 6 by the controller 23, automatic operation of the gene sequencing reaction device 1 may be realized, and the quality and efficiency of gene sequencing may be improved.

As shown in FIG. 1 to FIG. 3, the supporting platform 8 in the present embodiment includes a box. The aforementioned dipping container, the temperature control apparatus 5, the transfer apparatus 6, the chip supplying storage apparatus 14, the chip unloading storage apparatus 15, the container cover 4, the cover overturning mechanism 22, the air blowing apparatus 25 and the controller 23 are all disposed on a top face of the box. Reagents and tools and the like required for the gene sequencing reaction may also be stored and accommodated in the box. In order to facilitate the movement of the gene sequencing reaction device 1, rollers 27 are mounted below the cabinet.

In other embodiments not shown, the supporting platform 8 may also be a supporting plate.

As shown in FIG. 1 to FIG. 3, in the present embodiment, the gene sequencing reaction device 1 may include a signal lamp 28 for alarming when the gene sequencing reaction device 1 is abnormal.

In the present embodiment, a chemical reagent for gene sequencing reaction is loaded in each dipping reaction area, the transfer apparatus 6 holds a group of sequencing chips 2 for dipping the same in a group of dipping reaction areas for a period of time, then transfers the group of sequencing chips 2 into the next group of dipping reaction areas to be dipped for a period of time, and the circulation is accordingly. After any one of the group of sequencing chip 2 is dipped in the plurality of dipping reaction areas, once sequencing reaction process may be completed.

For example, in the embodiment shown in FIG. 1 to FIG. 3, each three sequencing chips are clamped as a group and may be numbered as No. 1 chip, No. 2 chip and No. 3 chip from right to left, the dipping cylinders 3 are sequentially numbered from right to left to the last one starting from the back row, and are sequentially numbered from left to right to the last one starting from the front row, which are respectively No. 1 dipping cylinder (the rightmost side on the back row), No. 2 dipping cylinder, No. 3 dipping cylinder, . . . , No. 17 dipping cylinder (the leftmost side on the back row), No. 18 dipping cylinder (the leftmost side on the front row), No. 19 dipping cylinder, . . . , No. 34 dipping cylinder (the rightmost side on the front row). When the gene sequencing reaction is started, the No. 3 chip is dipped in the No. 1 dipping cylinder; after being dipped for a predetermined time, the No. 3 chip is transferred into the No. 2 dipping cylinder to be continuously dipped, meanwhile, after the No. 2 chip is dipped in the No. 1 dipping cylinder for the predetermined time, the No. 3 chip is transferred into the No. 3 dipping cylinder to be continuously dipped, meanwhile, the No. 2 chip is dipped in the No. 2 dipping cylinder to be continuously dipped, and the No. 1 chip is dipped in the No. 1 dipping cylinder to start dipping. And so on, after a group of chips is dipped in a group of dipping cylinders, the sequencing chips 2 are sequentially transferred into the dipping cylinders with numbers greater than the respective dipping cylinders by 1 to be continuously dipped, until corresponding dipping processes of all sequencing chips 2 in the dipping cylinders are completed. The dipping processes in the No. 16 to No. 17 dipping cylinders, the No. 18 to No. 19 dipping cylinders and the No. 33 to No. 34 dipping cylinders are similar to the dipping processes in the No. 1 to No. 2 dipping cylinders, and a part of the sequencing chips 2 are dipped, while a part of the sequencing chips 2 is not dipped.

In some embodiments, one or more dipping cylinders at the head and/or the tail of at least one row of dipping cylinders (the specific number may be set according to the number of sequencing chips clamped every time) may be set as empty containers, or are filled with the same chemical reagent as the adjacent dipping cylinder or are filled with reagents that have no effect on the gene sequencing reaction, so that the sequencing chip 2 that does not participate in the dipping is also in the dipping cylinder.

In some embodiments, the dipping cylinders (or the dipping reaction areas) may also be grouped, for example, the dipping cylinders (or the dipping reaction areas) may be grouped according to the number of sequencing chips clamped every time, and each group of dipping cylinders (or the dipping reaction areas) holds the same chemical reagent, and during every dipping, a group of sequencing chips is dipped in a group of dipping cylinders holding the same chemical reagent. This setup may improve the efficiency of the gene sequencing reaction, but requires more dipping cylinders (or dipping reaction areas).

A gene sequencing system of the present embodiment includes a DNA sample loading device and a gene sequencing reaction device 1, and the gene sequencing reaction device 1 is the aforementioned gene sequencing reaction device 1.

A gene sequencing reaction method of the present embodiment includes: adding a chemical reagent for gene sequencing reaction into a dipping reaction area of a dipping container; controlling the temperature of the chemical reagent in the dipping reaction area; and dipping a sequencing chip 2 having a DNA sample loading structure on the surface and having a DNA sample loaded thereon in the chemical reagent for a predetermined time, and taking out the sequencing chip.

Optionally, different chemical reagents for gene sequencing reaction are injected in a plurality of dipping reaction areas, and the sequencing chip 2 is sequentially dipped in the plurality of dipping reaction areas for a predetermined time according to a predetermined sequence.

The working process of performing a gene sequencing reaction by using the gene sequencing reaction device 1 and the gene sequencing reaction method in the above embodiments will be briefly described below with reference to FIG. 1 to FIG. 3.

1. At an initial state, the chemical reagent for gene sequencing reaction is added into the dipping cylinders 3, the heat conduction liquid in the water bath kettle is adjusted to a suitable temperature, the sequencing chips 2 on which the gene sequencing reaction is about to be performed are mounted on the chip frameworks 9, all chip frameworks 9 are contained in the chip supplying storage apparatus 14.

2. The clamping jaws 7 of the transfer apparatus 6 clamp the chip frameworks 9 and dip the chip frameworks 9 in the dipping cylinders 3 for a period of time one by one; when the chip frameworks 9 are completely dipped in a row of dipping cylinders 3, the longitudinal movement mechanism 20 drives the lateral movement mechanism 19 to perform longitudinal movement, so that the chip frameworks 9 may be dipped in other row of dipping cylinders 3 one by one, until the chip frameworks 9 are dipped in all dipping cylinders 3.

3. After the chip frameworks 9 are dipped in all dipping cylinders 3, the transfer apparatus 6 places the chip frameworks 9 in the chip unloading storage apparatus 15, and DNA samples on the sequencing chips 2 complete the sequencing reaction process and wait for removal.

After the DNA samples on the sequencing chips 2 complete the sequencing reaction process, the DNA samples are transferred to an optical imaging device for imaging.

It should be understood that, the above steps are only one of the working processes that may be implemented by the gene sequencing reaction device 1, it does not indicate that the gene sequencing reaction device 1 may only implement these steps, nor is intended to limit the protection scope of the present disclosure. In addition, since the chemical reaction involved in the present disclosure does not belong to the content claimed in the present disclosure, and the non disclosure of the content does not affect the understanding of the present disclosure by those skilled in the art, therefore above chemical reaction is not disclosed herein.

The gene sequencing system and the gene sequencing reaction method of the present disclosure have similar technical effects as the gene sequencing reaction device 1 of the present disclosure.

It can be seen according to the above descriptions, the above embodiments of the present disclosure may achieve at least one of the following technical effects:

The gene sequencing reaction device 1 may achieve the gene sequencing reaction in the dipping manner.

The sequencing chip 2 is dipped in the chemical reagents in different dipping reaction areas to complete various steps required for the sequencing reaction.

The chemical reagent in the dipping reaction area may be reused, thereby reducing the cost of consumables.

There is no problem of uneven liquid flow rate in the dipping manner, and bubbles are unlikely to be generated on the surface of the sequencing chip 2, so that a more uniform and sufficient chemical reaction may be ensured.

The sequencing chip 2 is subjected to uniform pressure and uniform heating in the dipping cylinder 3, thereby generating no deformation.

Multiple sequencing chips 2 may be dipped at the same time, thereby having the advantages of high throughput.

No complicated fluid system is needed, few parts and components are used, the assembly is easy, and the manufacturing cost is low.

The gene sequencing reaction device 1 is automatically controlled by the controller 23 to realize automatic operation.

Finally, it should be noted that the above-mentioned embodiments are merely used for illustrating the technical solutions of the present disclosure, rather than limiting them.

Although the present disclosure has been described in detail with reference to the foregoing embodiments, those of ordinary skill in the art to which the present disclosure belongs should understand that: modifications may still be made to the specific embodiments of the present disclosure, or equivalent substitutions may be made to a part of technical features, and these modifications and equivalent substitutions shall fall within the scope of the technical solutions claimed by the present disclosure.

The invention claimed is:

1. A gene sequencing reaction device, comprising:
a supporting platform;
a dipping container disposed on the supporting platform, wherein the dipping container has a dipping reaction area configured to hold a chemical reagent for gene sequencing reaction, so as to dip a sequencing chip having a DNA sample loading structure on the surface and having a DNA sample loaded thereon in the chemical reagent to perform a gene sequencing reaction;
a temperature control apparatus, configured to control the temperature of the chemical reagent in the dipping reaction area;
a transfer apparatus, configured to insert the sequencing chip into the dipping reaction area or pull out the sequencing chip from the dipping reaction area; and
a chip holding apparatus, comprising one or more chip mounting positions, wherein the sequencing chip is mounted on the chip mounting position so as to move the sequencing chip by moving the chip holding apparatus, the chip holding apparatus comprises a chip framework, one or more chip mounting positions are disposed on the chip framework, an upper end of the chip framework is provided with a jaw fitting opening, the transfer apparatus comprises a clamping jaw connected with the chip framework and a first movement mechanism in driving connection with the clamping jaw to change a working position of the clamping jaw, the clamping jaw comprises a positioning frame and a clamping block, the positioning frame is connected with the first movement mechanism, the clamping block is movably disposed on the positioning frame, the positioning frame is provided with a positioning hole for inserting the upper end of the chip framework, and the clamping jaw is clamped with the jaw fitting opening of the chip framework inserted into the positioning hole so as to clamp the chip framework.

2. The gene sequencing reaction device according to claim 1, wherein the gene sequencing reaction device comprises a plurality of dipping containers; and/or, the dipping container comprises a plurality of dipping reaction areas isolated from each other.

3. The gene sequencing reaction device according to claim 1, wherein the dipping container comprises an overflow port.

4. The gene sequencing reaction device according to claim 1, comprising:
a chip supplying storage apparatus, configured to contain the sequencing chip on which the gene sequencing reaction is about to be performed; and/or,
a chip unloading storage apparatus, configured to contain the sequencing chip on which the gene sequencing reaction has been completed.

5. The gene sequencing reaction device according to claim 4, wherein the chip supplying storage apparatus and/or the chip unloading storage apparatus comprises:

a chip storage box, wherein the top of the chip storage box is open and is provided with a slot and a drain hole, the slot is configured to position and contain the sequencing chip, and the drain hole is formed in a bottom wall of the chip storage box to discharge liquid in the chip storage box; and, a liquid storage box disposed below the drain hole for receiving the liquid discharged from the drain hole.

6. The gene sequencing reaction device according to claim 1, comprising a container cover being configured to be capable of being opened and closed and covered on the dipping container to prevent the evaporation of the chemical reagent.

7. The gene sequencing reaction device according to claim 6, wherein the container cover comprises a plurality of cover bodies, each of the cover bodies is correspondingly disposed with one or more dipping reaction areas to prevent the evaporation of the chemical reagent in the corresponding dipping reaction areas, and at least one of the cover bodies is opened and closed independently relative to other cover bodies.

8. The gene sequencing reaction device according to claim 6, comprising a cover overturning mechanism being in driving connection with the container cover to drive the container cover to open and close.

9. The gene sequencing reaction device according to claim 2, wherein the transfer apparatus comprises a connecting portion configured to be connected with the sequencing chip and a second movement mechanism being in driving connection with the connecting portion to change a working position of the connecting portion.

10. The gene sequencing reaction device according to claim 9, wherein the plurality of dipping reaction areas are disposed in one or more rows along a lateral direction; the second movement mechanism comprises a lateral movement mechanism, a longitudinal movement mechanism and a vertical movement mechanism, the longitudinal movement mechanism is disposed on the supporting platform, the lateral movement mechanism is disposed on the longitudinal movement mechanism, the vertical movement mechanism is disposed on the lateral movement mechanism, the connecting portion is disposed on the vertical movement mechanism, the longitudinal movement mechanism drives the lateral movement mechanism to perform longitudinal movement, the lateral movement mechanism drives the vertical movement mechanism to perform lateral movement, and the vertical movement mechanism drives the connecting portion to perform vertical movement.

11. The gene sequencing reaction device according to claim 1, wherein a first DNA sample loading structure is provided on a first side of the sequencing chip and a second DNA sample loading structure is provided on a second side of the sequencing chip; and the chip mounting position comprises a chip mounting opening, the sequencing chip is mounted in the chip mounting opening, and the chip mounting opening is a through opening with both open sides.

12. The gene sequencing reaction device according to claim 1, wherein a surface of the chip framework is a hydrophobic surface, and/or, a lower end of the chip framework is gradually tapered from top to bottom.

13. The gene sequencing reaction device according to claim 1, comprising a controller, wherein:

the controller is coupled with the temperature control apparatus to control the temperature of the chemical reagent; and/or, the controller is coupled with the transfer apparatus to control the dipping time and/or dipping sequence of the sequencing chip in the dipping reaction area.

14. The gene sequencing reaction device according to claim 1, comprising the sequencing chip, and the surface of the sequencing chip is provided with the DNA sample loading structure.

15. The gene sequencing reaction device according to claim 1, comprising a protective cover, and the dipping container is disposed in the protective cover.

16. The gene sequencing reaction device according to claim 1, comprising an air blowing apparatus, configured to blow off the chemical reagent on the surface of the sequencing chip and/or a surface of the chip holding apparatus on which the sequencing chip is mounted.

17. A gene sequencing reaction device, comprising:
a supporting platform;
a dipping container disposed on the supporting platform, wherein the dipping container has a dipping reaction area configured to hold a chemical reagent for gene sequencing reaction, so as to dip a sequencing chip having a DNA sample loading structure on the surface and having a DNA sample loaded thereon in the chemical reagent to perform a gene sequencing reaction;
a temperature control apparatus, configured to control the temperature of the chemical reagent in the dipping reaction area;
a transfer apparatus, configured to insert the sequencing chip into the dipping reaction area or pull out the sequencing chip from the dipping reaction area; and
a chip holding apparatus, comprising one or more chip mounting positions, wherein the sequencing chip is mounted on the chip mounting position so as to move the sequencing chip by moving the chip holding apparatus, wherein the chip holding apparatus comprises a chip framework, the chip mounting position is disposed on the chip framework, and a lower end of the chip framework is gradually tapered from top to bottom.

18. A gene sequencing reaction device, comprising:
a supporting platform;
a dipping container disposed on the supporting platform, wherein the dipping container has a dipping reaction area configured to hold a chemical reagent for gene sequencing reaction, so as to dip a sequencing chip having a DNA sample loading structure on the surface and having a DNA sample loaded thereon in the chemical reagent to perform a gene sequencing reaction;
a temperature control apparatus, configured to control the temperature of the chemical reagent in the dipping reaction area;
a transfer apparatus, configured to insert the sequencing chip into the dipping reaction area or pull out the sequencing chip from the dipping reaction area;
a chip supplying storage apparatus, configured to contain the sequencing chip on which the gene sequencing reaction is about to be performed; and/or
a chip unloading storage apparatus, configured to contain the sequencing chip on which the gene sequencing reaction has been completed;
wherein the chip supplying storage apparatus and/or the chip unloading storage apparatus comprises:
a chip storage box, wherein the top of the chip storage box is open and is provided with a slot and a drain hole, the slot is configured to position and contain the sequencing chip, and the drain hole is formed in a bottom wall of the chip storage box to discharge liquid in the chip storage box; and a liquid storage box disposed below the drain hole for receiving the liquid discharged from the drain hole.

* * * * *